United States Patent
Blum (10) Patent No.: US 8,142,406 B2
(45) Date of Patent: Mar. 27, 2012

(54) OSTOMY COUPLING

(75) Inventor: John L. Blum, Toms River, NJ (US)

(73) Assignee: ConvaTec Technologies Inc., Las Vegas, NV (US)

( * ) Notice: Subject to any disclaimer, the term of this patent is extended or adjusted under 35 U.S.C. 154(b) by 730 days.

(21) Appl. No.: 11/566,331

(22) Filed: Dec. 4, 2006

(65) Prior Publication Data

US 2007/0129695 A1 Jun. 7, 2007

Related U.S. Application Data (60) Provisional application No. 60/748,029, filed on Dec. 7, 2005.

(51) Int. Cl.
*A61F 5/44* (2006.01)

(52) U.S. Cl. ........ 604/338; 604/332; 604/337; 604/339; 604/341; 604/342

(58) Field of Classification Search .................. 604/388, 604/338, 332, 337, 339, 341, 342
See application file for complete search history.

(56) References Cited

U.S. PATENT DOCUMENTS

| 4,929,245 | A |   | 5/1990 | Holtermann |   |
|---|---|---|---|---|---|
| 5,041,102 | A | * | 8/1991 | Steer et al. | 604/338 |
| 5,180,377 | A | * | 1/1993 | Holtermann | 604/342 |
| 5,322,523 | A | * | 6/1994 | Olsen | 604/338 |
| 5,830,200 | A | * | 11/1998 | Steer et al. | 604/338 |
| 6,409,710 | B1 | * | 6/2002 | Holtermann | 604/342 |
| 6,723,079 | B2 | * | 4/2004 | Cline | 604/337 |
| 2001/0004687 | A1 | * | 6/2001 | Plass et al. | 604/338 |

FOREIGN PATENT DOCUMENTS

| EP | 0373782 | 6/1990 |
| FR | 2690333 | 10/1993 |
| WO | WO8701274 | 3/1987 |
| WO | WO9101118 | 2/1991 |

* cited by examiner

*Primary Examiner* — Tatyana Zalukaeva
*Assistant Examiner* — Ginger T Chapman
(74) *Attorney, Agent, or Firm* — Stuart E. Krieger

(57) ABSTRACT

An ostomy coupling including a body-side coupling member, an appliance-side coupling member including plural fastener lugs, and a bracing member. The lugs flex independently of each other to provide plural independent latching fastenings. The bracing member is moved between a bracing position in which the bracing member locks the lugs by resisting flexing movement, and a non-bracing or dismounted position in which the lugs are free to flex. The ostomy coupling is used with an ostomy pouch or with a controlled evacuation device.

8 Claims, 9 Drawing Sheets

OSTOMY COUPLING

FIELD OF THE INVENTION

The present invention relates to the field of ostomy couplings for releasably securing a body-side coupling element and an appliance-side coupling element. The ostomy appliance comprises, but is not limited to, a collection pouch, a stoma port (or plug or cap), or a controlled evacuation device.

BACKGROUND TO THE INVENTION

The majority of conventional ostomy couplings are either of the mechanical fastening type, or the adhesive fastening type. A mechanical interference fastening type is especially suitable where the advantage of a secure and positive mechanical fastening is desired.

Conventional ostomy couplings using a mechanical interference fastening generally comprise at least two coupling elements, one of which is, for example, a body-side coupling element for adhesive attachment to the body. The other coupling element is, for example, a non-body-side coupling element (also referred to as an appliance-side element), for example, a bag-side coupling element integrated with a collection pouch. The two coupling elements carry co-operating fasteners to allow the coupling elements to be repeatedly attached and separated, whereby the collection pouch is releasably attached and detached with respect to the body. Such an arrangement permits the body-side member to be worn on the body for a relatively long length of time, and permits frequent removal or changes of the operative part of the ostomy appliance without having to remove the body-side element. The term ostomy includes, but is not limited to, colostomy, ileostomy and urostomy.

Braced couplings are known, e.g., from U.S. Pat. No. 4,929,245 and EP-A-0373782. These specifications teach the use of bracing members that are rotatable relative to a coupling member to selectively brace coupling latches of the coupling member, depending on the rotational orientation.

One aspect of the present invention aims to provide a novel coupling structure that is easy to manufacture, simple to use in practice, allows for a low connection force, and also provides a secure engagement.

In another aspect, U.S. Pat. No. 6,723,079 describes a controlled evacuation device for enabling a wearer to control discharge of body waste from the stoma. Designing an ostomy coupling uniquely adapted for a controlled evacuation device provides different technical challenges from a conventional ostomy coupling. It would thus be desirable to provide a novel coupling that is suitable for a controlled evacuation device.

SUMMARY OF THE INVENTION

One aspect of the invention provides an ostomy coupling for releasably securing an ostomy appliance to a body, comprising a body-side coupling member and an appliance-side coupling member. The appliance-side coupling member comprises a plurality of lugs for forming an interference fit with the body-side coupling member. The lugs flex independently of each other. The coupling further comprises a bracing member for engaging the lugs to obstruct flexing of the lugs. The bracing member is mounted or mountable on the appliance-side coupling member. In one form, the bracing member is non-rotatable with respect to the appliance-side coupling member and/or the body-side coupling member. In another form, the bracing effect is independent of a rotational orientation of the bracing member.

The bracing member is movable in an axial direction relative to the appliance-side coupling member. The axial direction is defined to be generally parallel to an axis of a stomal orifice in the appliance-side coupling member.

The bracing member is movable with respect to the appliance-side coupling member between a bracing position and a substantially non-bracing position.

In the non-bracing position, the bracing member is disengaged from the appliance-side coupling member such that the bracing member is not directly connected to the appliance-side coupling member. The bracing member remains indirectly connected to, or captive relative to, the appliance-side coupling member via one or more intermediate attachments.

DETAILED DESCRIPTION OF THE INVENTION

Referring to FIGS. 1 to 4, a first embodiment of an ostomy coupling 10 generally comprises a body-side coupling member 12 and an appliance-side coupling member 14. The ostomy coupling 10 is intended for releasably attaching an ostomy appliance (not shown) to the user's skin. The body-side coupling member 12 remains in position on the skin for longer duration than the normal duration of use of the appliance. The appliance may be attached, removed, replaced or exchanged by means of the appliance-side coupling member 14 that forms a releasable mechanical fastening with the body-side coupling member 12. The ostomy appliance, for example, may include a collection pouch or a stoma port or plug, or a controlled evacuation device.

Figure 1:
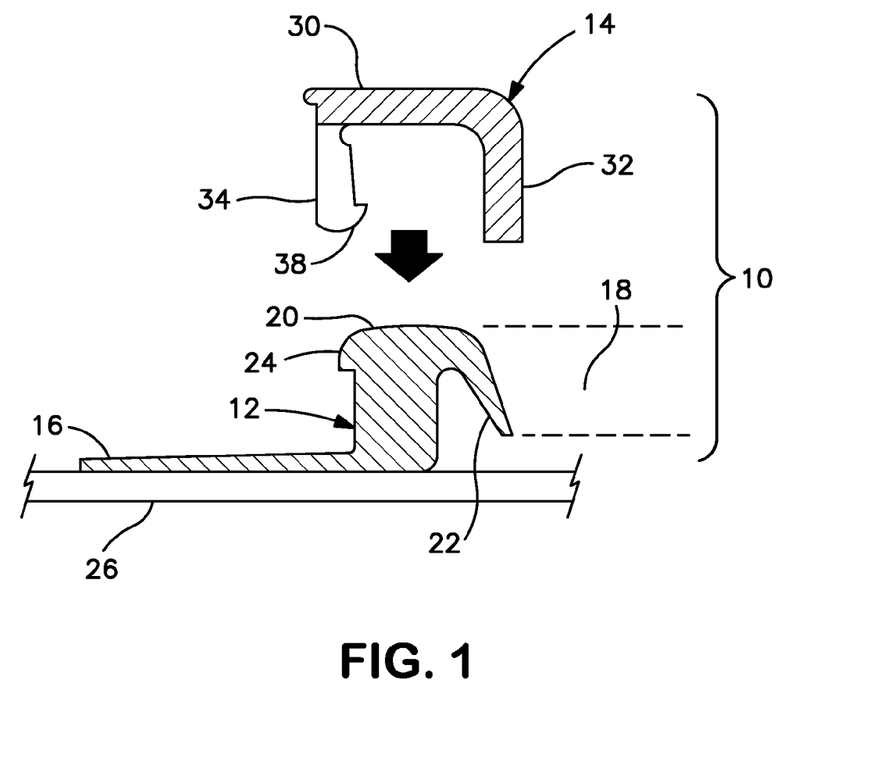
FIG. 1 is a schematic cross-sectional view of a first embodiment of anostomy coupling prior to attachment.

The body-side coupling member 12 generally comprises a flange 16 having a stomal opening 18 and an upstanding rib 20. The upstanding rib 20 includes a generally inwardly directed sealing wiper 22, and a generally outwardly directed undercut 24. The flange 16 is attached permanently to a pad of a skin friendly adhesive 26 by which the body-side coupling member is adhesively attached to the wearer's skin.

Figure 3:
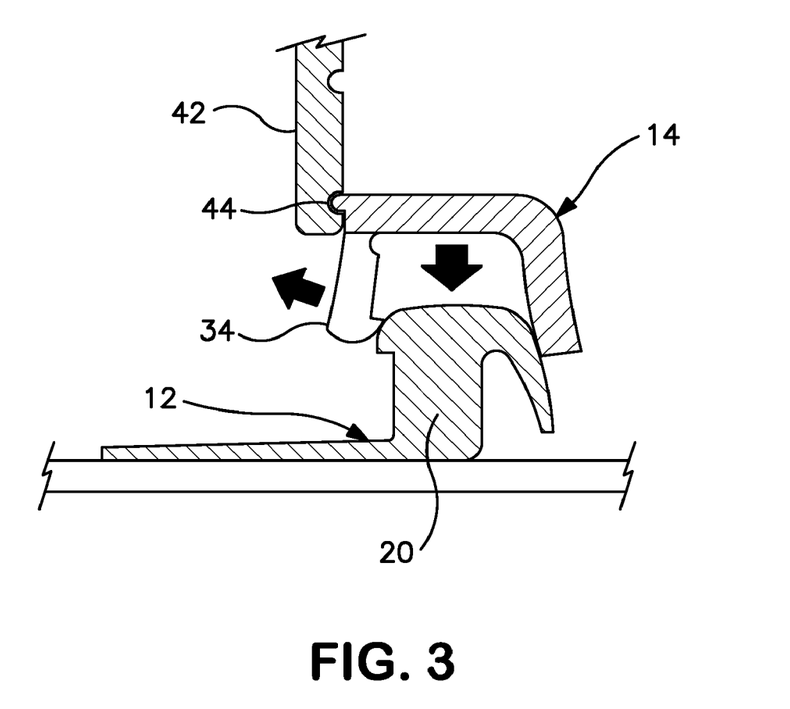
FIG. 3 is a schematic cross-sectional view of a partial attachment of the coupling members of FIG. 1.
Figure 4:
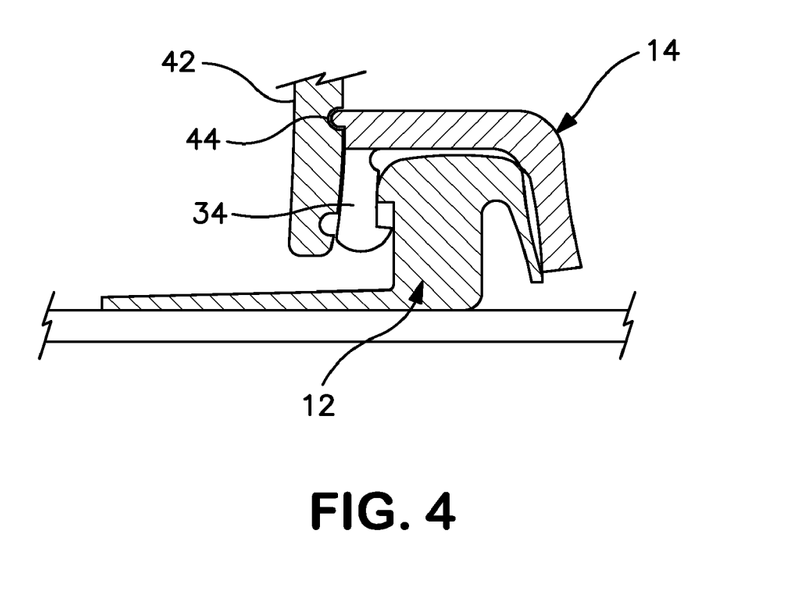
FIG. 4 is a schematic cross-sectional view of a full attachment of the coupling members of FIG. 1.
Figure 7:
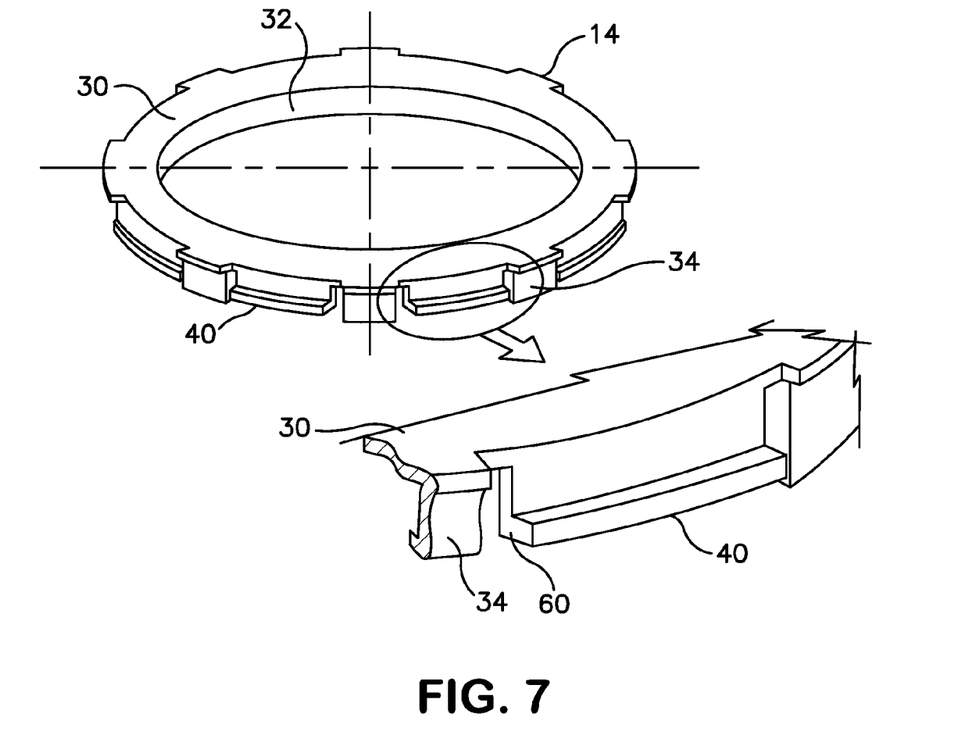
FIG. 7 is a perspective view of a fourth embodiment showing an appliance-side coupling member in isolation.
Figure 7A:
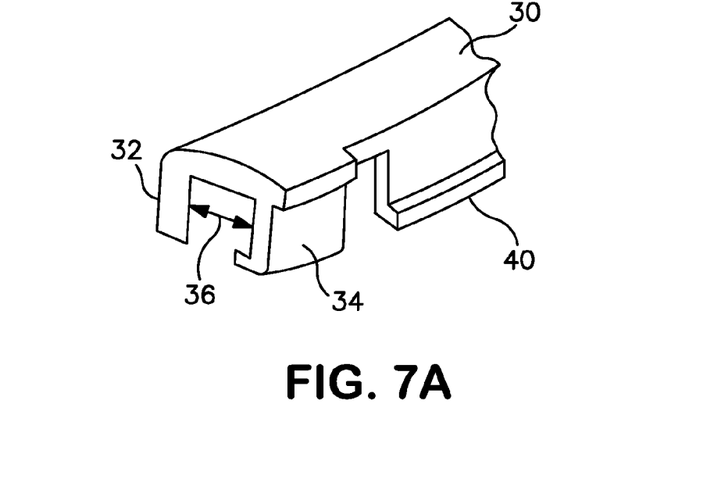
FIG. 7a is an enlarged partial schematic view of the inset of FIG. 7.

The appliance-side coupling member 14 includes an annular profile having a rear wall 30 from which projects a generally cylindrical wall 32 and/or a plurality of lugs 34. The lugs 34 and the cylindrical wall 32 together define a clearance or rebate 36 (see FIG. 7a) for receiving the upstanding rib 20 when the coupling members 12, 14 are pressed into mutual engagement as depicted in FIGS. 3 and 4. The cylindrical wall 32 provides a seal surface against which the seal wiper 22 of the upstanding rib 20 seats to provide a substantially liquid tight and/or substantially gas tight ring seal.

Each lug 34 carries a latching undercut 38 on its surface facing towards the cylindrical wall 32, for interference fit or latching engagement with the upstanding rib 20. The segmentation of the appliance-side coupling member 14 into independent fastener lugs 34 enables each fastener lug 34 to flex generally independently of the other lugs 34. Each lug 34 acts like a separate leaf spring depending from the rear wall 30. Such independent flexing generally enables the coupling members 12, 14 to be pressed together using only a relatively light compression force, because torsional stress and stretching associated with a continuous cylindrical wall 32 carrying the latches 38 is avoided. The independence of the lugs 34 also provides more predictable or controllable detachment of one coupling member relative to the other. For example, disengagement of one lug 34 from the upstanding rib 20 does not, in general, affect engagement of the other lugs 34 with the upstanding rib 20. Thus, accidental disengagement of one of the lugs 34 during use does not, in general, risk disengagement of the other lugs 34. This avoids the risk of "unzipping" or progressive peeling apart that can sometimes occur with certain other types of ostomy couplings should the coupling accidentally become disengaged in a small localized area. The security of the coupling 10 is controlled by adjusting the size and profiles of the undercuts 24, 38, and the stiffness (e.g., thickness) of each lug 34. There may be, to some extent, a relationship between the application force (e.g., the force needed to assemble the coupling members into engagement) and coupling security in mechanical coupling systems. However, the creation of the independent lugs 34 significantly decouples these two characteristics. It may also be appreciated that the creation of independent lugs 34 does not reduce the seal integrity of the coupling 10, as the seal is formed between the cylindrical wall 32 and the sealing wiper 22, which may both be continuous surfaces.

Figure 2:
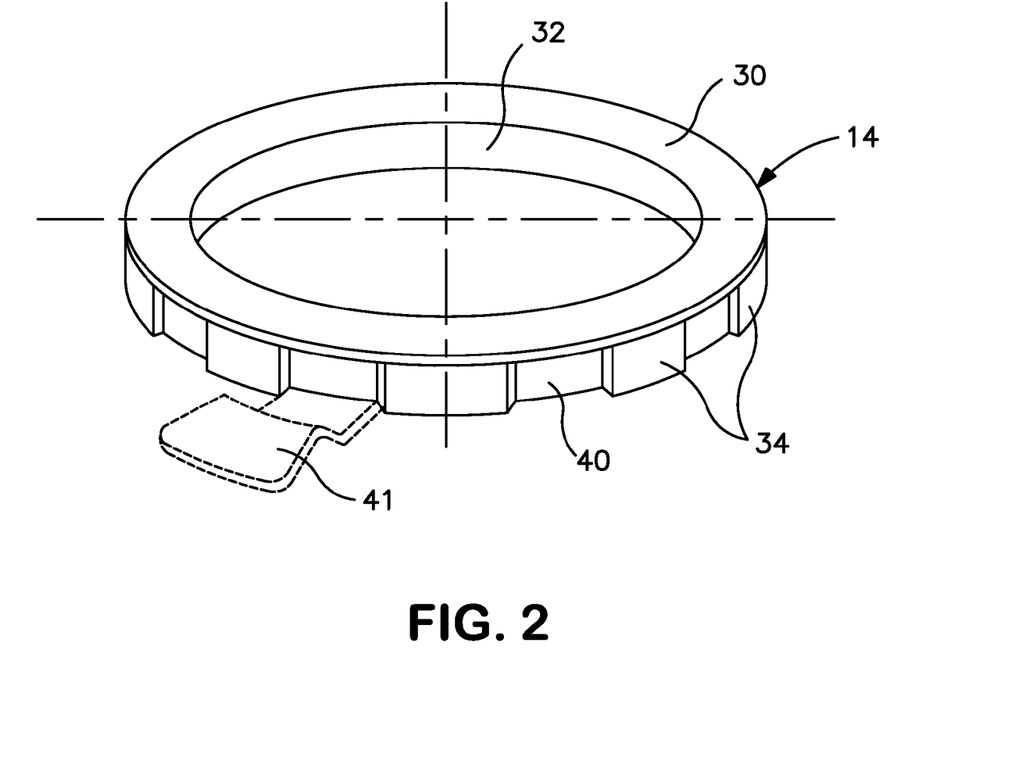
FIG. 2 is a perspective view of an appliance-side coupling member of FIG. 1 in isolation.

Referring to FIG. 2, the appliance-side coupling member 14 optionally comprises depending outer wall segments 40 positioned between adjacent lugs 34. The wall segments 40 depend from the rear wall 30 to a lesser extent than the lugs 34. The lugs 34 flex independently of the wall segments 40. The wall segments 40 do not include any undercut or latch facing towards the rib 20, and do not positively engage the upstanding rib 20. Instead, the wall segments 40 act as abutments or guides to help stabilize and center the appliance-side coupling member 14 relative to the body-side coupling member 12.

The appliance-side coupling member 14 further comprises a tab (indicated in phantom at 41) projecting outwardly and by which a user grips the appliance-side coupling member 14 to pull or peel the appliance-side coupling member 14 from the body-side coupling member 12. The tab 41 projects from one of the lugs 34, in order to apply a flexing force directly to the lug 34. Alternatively (as illustrated in FIG. 2), the tab 41 projects from a position between two adjacent lugs 34. For example, the tab 41 projects from a wall segment 40.

A bracing member 42 is mounted or mountable on the appliance-side coupling member 14. The bracing member 42 is movable into a bracing position as shown in FIG. 4. In the bracing position, the bracing member 42 braces the lugs 34 to resist outward flexing of the lugs 34. In one form, the bracing member 42 directly contacts the lugs 34 to apply continuous static pressure, and thereby increase the contact force between the lugs 34 and the upstanding rib 20. Alternatively, the bracing member 42 may be dimensioned and positioned such that bracing contact may occur only when the lug 34 commences to flex outwardly from a normal position. In either case, the bracing member 42 acts as a locking device for locking the lugs 34 against disengagement. The bracing member 42 may be configured such that the bracing member 42 is not rotatable relative to one or both of the coupling members 12, 14. Alternatively, the bracing member 42 may be configured such that the bracing effect is independent of a rotational orientation of the bracing member 42. (See FIGS. 3,4 and 9a)

The coupling 10 is configured such that the coupling members 12, 14 are assembled even when the bracing member 42 is in the bracing position, or the coupling 10 may be configured such that the bracing member 42 should not adopt the bracing position during assembly of the coupling members 12, 14. In the present embodiment, as illustrated in FIGS. 1 and 3, the bracing member 42 is initially disposed out of the bracing position to allow assembly using only a light connection force, and as illustrated in FIG. 4, the bracing member 42 is moved to the bracing position once the coupling members 12, 14 have been assembled together.

In order to separate coupling members 12, 14, the user moves the bracing member 42 out of the bracing position, so that the lugs 34 flex without external resistance. The bracing member 42 is dismounted from the appliance-side coupling member 14.

Figure 5:
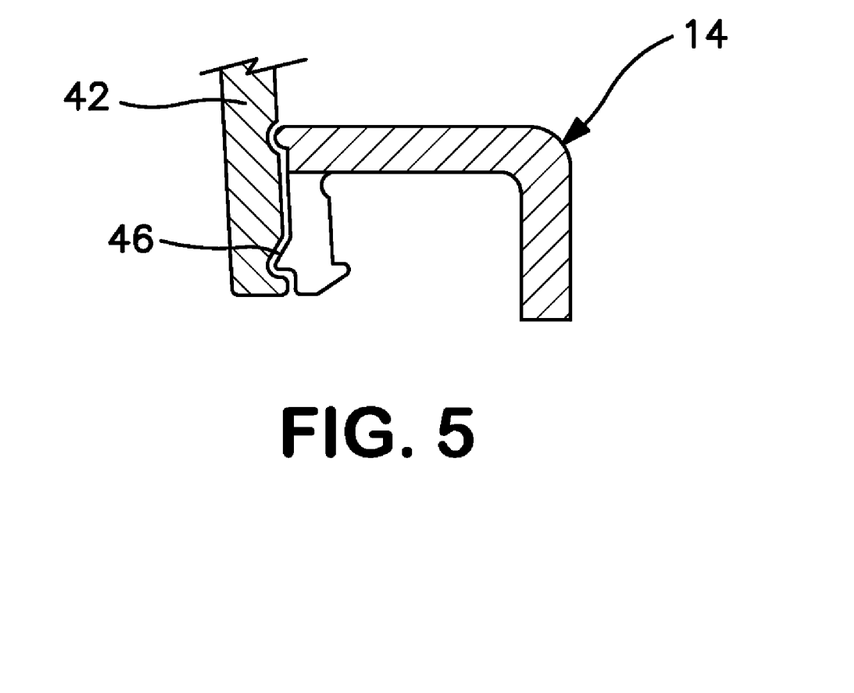
FIG. 5 is a schematic cross-sectional view of a second embodiment showing an appliance-side coupling member.

The bracing member 42 comprises, for example, a collar, skirt or band that encircles the lugs 34. The bracing member 42 is retained in the bracing position by friction, or one or more catches or detents 44 are provided to define the bracing position, and/or a non-bracing position, more positively. A shallow detent 44 requires only modest force from the user to move the bracing member 42 out of the detained position. One or more larger, or more aggressive, catches or detents 44 anchors the bracing member 42 more strongly, and requires a greater force to move the bracing member 42 out of its bracing position before the coupling members 12, 14 may be separated. For example, FIG. 5 illustrates a second embodiment including a more aggressive interlock between the bracing member 42 and the appliance-side coupling member 14 when the bracing member 42 is in the bracing position. The bracing member 42 comprises one or more latches and/or undercuts 46 for engaging a portion of each lug 34. The latches 46 are segmented or may be continuous around an inner surface of the bracing member 42. The latches 46 engage an extremity of each lug 34.

Figure 6:
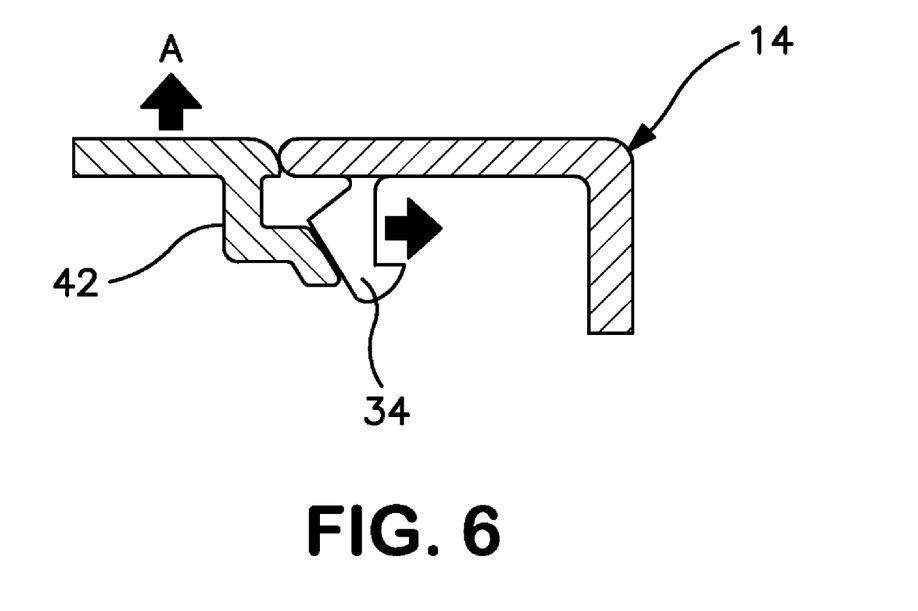
FIG. 6 is a schematic cross-sectional view of a third embodiment showing an appliance-side coupling member.

In the foregoing embodiments, the bracing member 42 is configured to be movable into the bracing position by movement in a generally axial direction towards the body-side coupling member 12. However, in an alternative embodiment illustrated in FIG. 6, the bracing member 42 is configured to be moved in a direction generally axially away (Arrow "A")

from the body-side coupling member 12, to arrive at the bracing position. In FIG. 6, the bracing member 42 and the lugs 34 are shaped such that movement of the bracing member 42 away from the body-side coupling member 12 (arrow "A") tightens the bracing effect on the lugs 34. Such an arrangement is useful when it is desired that the coupling 10 tightens when an attempt is made to pull the bracing member 42 away from the body. Although not shown explicitly in FIG. 6, detent 44 and/or catch features may be provided to hold the bracing member 42 in the bracing and/or non-bracing positions.

Figure 8:
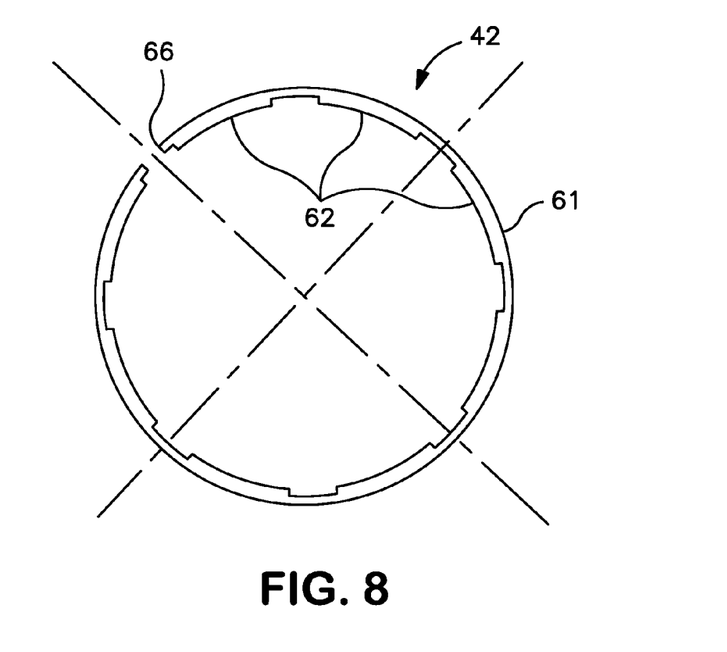
FIG. 8 is a schematic elevational view of the underside of the bracing member of the fourth embodiment in isolation.
Figure 9:
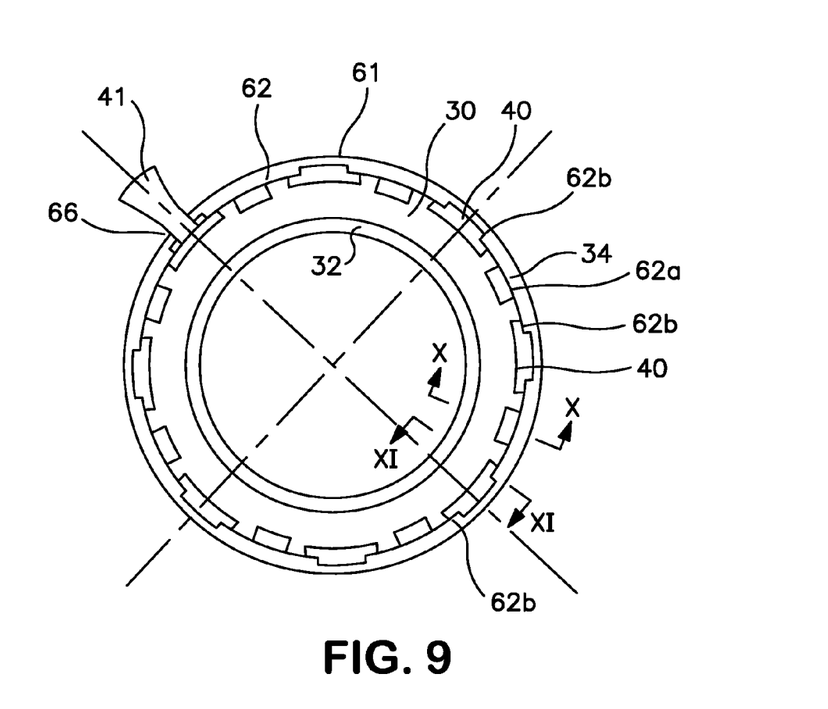
FIG. 9 is a schematic elevational view of the underside of the bracing member of FIG. 8 in a bracing position with respect to the appliance-side coupling member of FIG. 7.
Figure 9A:
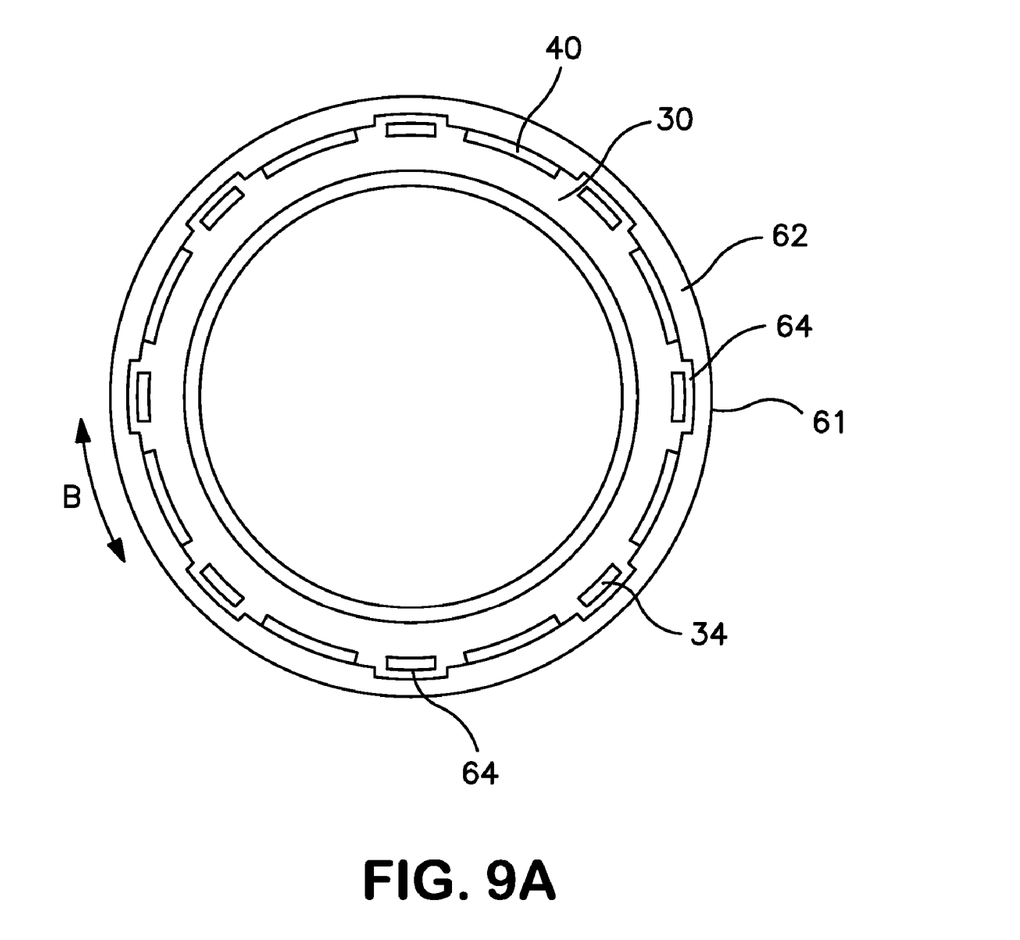
FIG. 9a is a schematic elevational view of a fifth embodiment of a bracing member in a flex position.

Referring to FIGS. 7-11, a fourth embodiment is illustrated in FIGS. 7, 8, 9, 10 and 11 and a fifth embodiment is illustrated in FIG. 9a. The appliance-side coupling member 14 is similar to that of the first embodiment. The number of lugs 34 may vary according to the size and intended application. However, typically, between 4 and 12 lugs 34 are used, for example, about 8. The wall segments 40 define a step profile 60 with respect to the rear wall 30. The wall segments 40 project radially outwardly also with respect to the radially outer surface of each lug 34.

Figure 10:
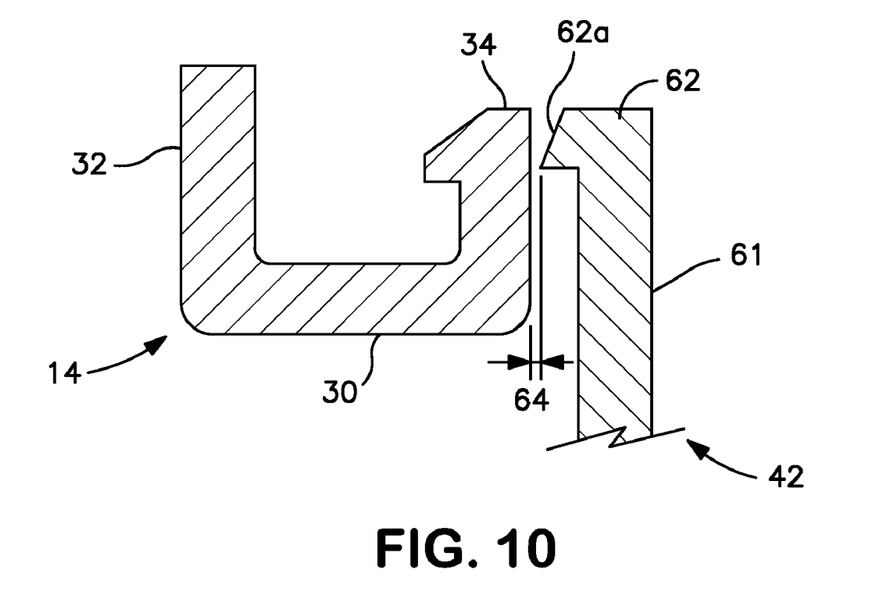
FIG. 10 is a schematic cross sectional view along the line X-X of FIG. 9.

Referring to FIGS. 8, 9 and 9a, the bracing member 42 comprises a generally cylindrical wall 61. A plurality of latches 62 are formed at or near the lower extremity of the cylindrical wall 61. Each latch 62 has an arcuate length greater than the arcuate length of each lug 34. The number of latches 62 are the same as the number of lugs 34. Each latch 62 performs a dual function when the bracing member 42 is in the bracing position on the appliance-side coupling member 14. Referring to FIGS. 9, 9a and 10, one function is for a central region of each latch 62 to act as a brace surface 62a for a respective lug 34. The brace surface 62a lies radially outside the lug 34 in order to resist outward flexing of the lug 34. The brace surface 62a presses against the lug 34 in order to increase the static fastening force of the lug 34. Alternatively, there may be a small clearance 64 between the lug 34 and the brace surface 62a. The clearance 64 allows a small degree of flexing of the lug 34 before further flexing of the lug 34 is restricted by contact with the brace surface 62. The clearance 64 is useful for applications in which it is desired to permit the appliance-side coupling member 14 to be fitted to the body-side coupling member 12 with the bracing member 42 already in its bracing position, as the clearance 64 permits the coupling members 12, 14 to be assembled without too great an application force.

Figure 11:
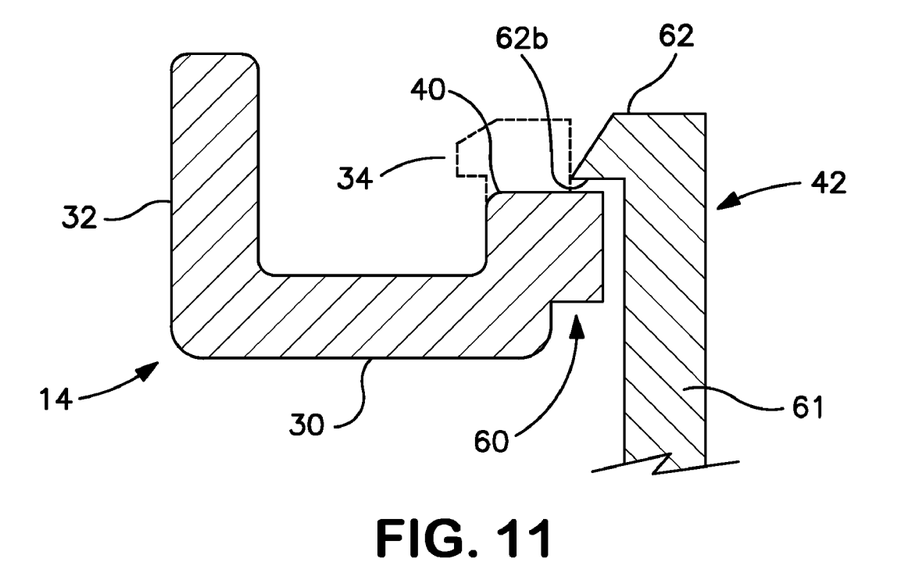
FIG. 11 is a schematic cross-sectional view along the line XI-XI of FIG. 9.

Referring to FIGS. 9, 9a and 11, another function of the latch 62 is for end regions 62b to mate with respective wall portions 40 of the wall segments 40 to retain the bracing member 42 in the bracing position on the appliance-side coupling member 14. In use, when it desired to release the bracing effect, the bracing member 42 is pulled or peeled from the appliance-side coupling member 14 by applying sufficient force to overcome the mating engagement of the end regions 62b of the latches 62 and the wall portions 40b of the wall segments 40.

In the present embodiment, the bracing effect depends on the relative rotational alignment of the latches 62 and the lugs 34, as illustrated in FIG. 9. Mechanical keying is used to ensure that the bracing member 42 has a correct rotational alignment or orientation with respect to the appliance-side coupling member 14. For example, the tab 41 is received in a gap or recess 66 provided in the cylindrical wall 61. With such an arrangement, the bracing member 42 is not rotatable, at least when in the bracing position. In an alternative form, the bracing effect may be made independent of rotational alignment of the bracing member 42, for example, by modifying the latches 62 to form a continuous annular latch surface as illustrated in FIG. 9a. FIG. 9a shows that the bracing member 42 may be rotated in the directions of Arrow B. when the bracing member 42 is rotated to the position where the latches 62 are spaced from the lugs 34, the lugs 34 may flex. When the bracing member 42 is rotated so that the latches 62 are behind the lugs 34 the flex by the lugs 34 is prevented.

Figure 12:
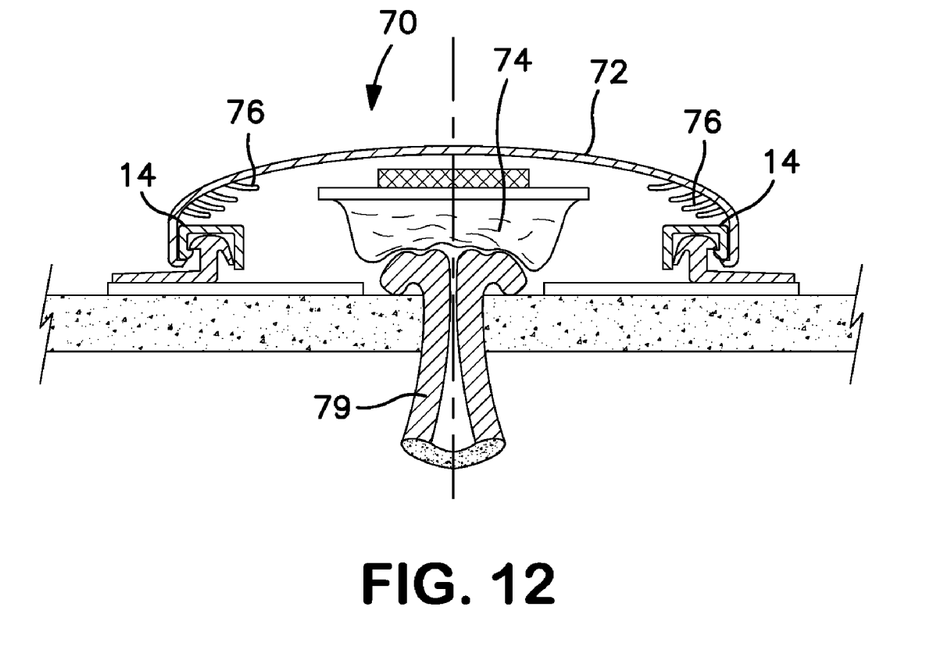
FIG. 12 is a schematic cross-sectional view of a sixth embodiment showing a coupling used with a controlled evacuation device with the stoma seal in contact with the stoma.
Figure 13:
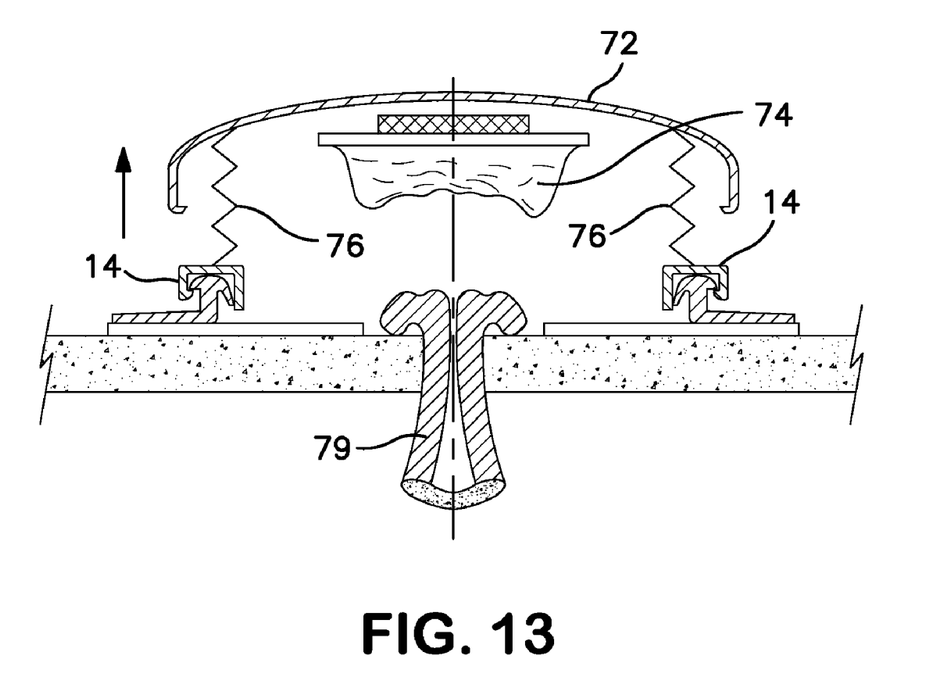
FIG. 13 is a schematic cross-sectional view of a sixth embodiment showing a coupling used with a controlled evacuation device with the stoma seal apart from the stoma.

FIG. 12 illustrates the suitability of coupling 14 for use with a controlled evacuation device 70. Constructional details of an example controlled evacuation device is found in U.S. Pat. No. 6,723,079, the contents of which are hereby incorporated by reference. The controlled evacuation device 70 comprises a cap 72 carrying a stoma seal 74, and a collection tube 76 extending between the cap 72 and the appliance-side coupling member 14 that is integrated in the controlled evacuation device 70. The controlled evacuation device 70 generally adopts one of two operation states. In a first operation state (as shown in FIG. 12) the cap 72 is directly mounted on the appliance-side coupling member 14, the collection tube 76 is generally collapsed, and the stoma seal 74 is presented for contacting the stoma 79 when the device is worn on the body. In a second operation state (See FIG. 13), the cap 72 is dismounted and moved away from the appliance-side coupling member 14, thus moving the seal 74 away, and extending the collection tube 76. In the second operation state, the cap 72 remains indirectly attached to the appliance-side coupling member 14 via the collection tube 76. The bracing member 42 is implemented as a portion of the cap 72 for engaging the appliance-side coupling member 14 when the controlled evacuation device 70 is in the first operation state. In the first operation state, the controlled evacuation device 70 requires a secure mechanical fastening to the body-side coupling member 12 in order to provide a secure support for the stoma seal 74. In the second operation state, the controlled evacuation device 70 is ready for removal from the body-side coupling member 12. The dismounting of the bracing member 42 when in the second operation state facilitates easy removal of the appliance-side coupling member 14 from the body-side coupling member 12.

It will be appreciated that the foregoing description is illustrative of preferred forms of the invention, and that many modifications, improvements and equivalents are possible that are within the scope of the claimed coverage of the invention.

The invention claimed is:

1. An ostomy appliance coupling comprising:
   a. a body-side coupling member;
   b. an appliance-side coupling member capable of coupling to and decoupling from the body-side coupling member, the appliance-side coupling member including a plurality of flexible fastener lugs for latching engagement with the body-side coupling member, each of said fastener lugs being capable of flexing independently of the other lugs;
   c. an annular, continuous, non-dynamic, and integral bracing member on the body-side coupling member moveable so as to be positionable in a bracing position or a non-bracing position, in a bracing position the bracing member braces said flexible fastener lugs so as to resist outward flexing of the flexible lugs and brace said appliance-side and body-side coupling members together, in a non-bracing position the bracing member is demounted from the appliance-side coupling member so as not to brace the flexible fastener lugs and permit decoupling of the coupling members; and
   d. a grippable tab projecting outwardly from said bracing member proximate to at least one fastener lug, said tab being grippable and manipulatable for applying a flexing force to said at least one fastener lug for separating the appliance-side coupling member from said body-side coupling member.

2. The ostomy appliance coupling according to claim 1, wherein each of the flexible fastener lugs comprises a latch profile.

3. The ostomy appliance coupling according to claim 1, further comprising a positive engagement device for positively retaining the bracing member in a bracing position on the appliance-side coupling member.

4. The ostomy appliance coupling according to claim 3, wherein the positive engagement device comprises co-operating surfaces of the bracing member and the appliance-side coupling member.

5. The ostomy appliance coupling according to claim 4, wherein the co-operating surface of the appliance-side coupling member is a surface of a respective lug.

6. The ostomy appliance coupling according to claim 4, wherein the appliance-side coupling member comprises a wall segment between adjacent lugs, and wherein the co-operating surface of the appliance-side coupling member is a surface of the wall segment.

7. The ostomy appliance coupling according to claim 6, wherein said surface of the wall segment projects radially of the adjacent lugs.

8. The ostomy appliance coupling according to claim 7, wherein said co-operating surface of the bracing member comprises a projection having an arcuate length longer than an arcuate length of each lug.

* * * * *